(12) United States Patent
Ruiz Vico

(10) Patent No.: US 10,041,246 B2
(45) Date of Patent: Aug. 7, 2018

(54) SPRAYABLE, THERMAL AND ACOUSTIC INSULATING SURFACING

(71) Applicant: INDUSTRIAS KOLMER, S.A., Granada (ES)

(72) Inventor: Joaquin Ruiz Vico, Granada (ES)

(73) Assignee: INDUSTRIAS KOLMER, S.A., Granada (ES)

( * ) Notice: Subject to any disclaimer, the term of this patent is extended or adjusted under 35 U.S.C. 154(b) by 0 days.

(21) Appl. No.: 15/222,386

(22) Filed: Jul. 28, 2016

(65) Prior Publication Data

US 2017/0204278 A1 Jul. 20, 2017

Related U.S. Application Data

(63) Continuation-in-part of application No. 14/254,909, filed on Apr. 17, 2014, now abandoned.

(30) Foreign Application Priority Data

Jul. 4, 2013 (ES) .................................. 201331006

(51) Int. Cl.

| | | |
|---|---|---|
| *E04B 1/88* | (2006.01) | |
| *E04B 1/76* | (2006.01) | |
| *C09D 197/00* | (2006.01) | |
| *C08L 97/02* | (2006.01) | |
| *C09D 5/00* | (2006.01) | |
| *C09D 5/14* | (2006.01) | |
| *A01N 43/70* | (2006.01) | |
| *C09D 133/02* | (2006.01) | |
| *C09D 133/12* | (2006.01) | |
| *C09D 133/08* | (2006.01) | |
| *C08L 33/08* | (2006.01) | |
| *E04B 1/74* | (2006.01) | |
| *C09D 7/61* | (2018.01) | |
| *C09D 7/63* | (2018.01) | |
| *C09D 7/65* | (2018.01) | |
| *C08K 5/41* | (2006.01) | |
| *C08K 3/34* | (2006.01) | |
| *C08K 5/3492* | (2006.01) | |
| *C08K 5/47* | (2006.01) | |
| *E04F 13/02* | (2006.01) | |

(52) U.S. Cl.
CPC ................ *E04B 1/88* (2013.01); *A01N 43/70* (2013.01); *C08L 33/08* (2013.01); *C09D 5/00* (2013.01); *C09D 5/14* (2013.01); *C09D 7/61* (2018.01); *C09D 7/63* (2018.01); *C09D 7/65* (2018.01); *C09D 133/02* (2013.01); *C09D 133/08* (2013.01); *C09D 133/12* (2013.01); *E04B 1/74* (2013.01); *C08K 3/34* (2013.01); *C08K 5/3492* (2013.01); *C08K 5/41* (2013.01); *C08K 5/47* (2013.01); *E04B 2001/745* (2013.01); *E04F 13/02* (2013.01)

(58) Field of Classification Search
CPC ...... C08L 97/02; C08L 2205/02; C08L 33/08; C08L 1/02; C08L 1/12; C08L 29/04; C08L 2201/54; C09D 133/08; C09D 133/00; C09D 197/00; C09D 7/125; B32B 2307/304; B32B 9/02; E04B 1/762; E04B 1/88; C04B 2111/52; B29K 2995/0015; E04C 2/288
USPC ........................................................... 252/62
See application file for complete search history.

(56) References Cited

U.S. PATENT DOCUMENTS

| | | | | |
|---|---|---|---|---|
| 5,505,344 A | * | 4/1996 | Woods ..................... | B05D 5/00 106/122 |
| 2009/0156399 A1 | * | 6/2009 | Hungenberg .......... | A01N 47/34 504/100 |
| 2010/0264353 A1 | * | 10/2010 | Hartmann ............... | C08B 15/02 252/62 |
| 2012/0071324 A1 | * | 3/2012 | Uhr ......................... | A01N 25/10 504/158 |
| 2013/0045241 A1 | * | 2/2013 | Premachandran ..... | A01N 47/04 424/400 |

* cited by examiner

*Primary Examiner* — Matthew E. Hoban
*Assistant Examiner* — Lynne Edmondson
(74) *Attorney, Agent, or Firm* — Hoglund & Pamias, PSC; Roberto J. Rios

(57) ABSTRACT

The present invention relates to a sprayable, thermal and acoustic insulating surfacing based on cork and applicable on façades and walls or ceilings, both indoors and outdoors, consisting of a binding aqueous dispersion including: acrylic copolymer; polyvinyl alcohol; sodium carboxymethyl cellulose; ultrafine talcum powder; wetting agents and surfactants; preservative; terbutryn with 3-iodo-2-propynyl butylcarbamate;
and water.

7 Claims, No Drawings

SPRAYABLE, THERMAL AND ACOUSTIC INSULATING SURFACING

FIELD OF THE INVENTION

The field of application of the present invention is comprised within the construction sector, focusing on the field of indoor and outdoor surfacing, particularly including sprayed surfacing products or materials.

BACKGROUND OF THE INVENTION

In relation to the current state of the art, it should be mentioned that although different types of materials and products for being used as surfacing are known, including some which are applied by means of a spraying method, thus far the applicant is unaware of any such product having technical, structural or constitutive features similar to those of the surfacing based on cork herein proposed and claimed.

SUMMARY OF THE INVENTION

As expressed in the title of the present specification, the invention relates to a sprayable, thermal and acoustic insulating surfacing, which contributes to the function for which it is intended several novelty features and advantages that will be described in detail below and which entail an improved alternative to the systems known today for the same purpose.

More particularly, the object of the invention focuses on a sprayable surfacing based on cork which consists of an aqueous product containing natural cork particles and developed for being used as surfacing for façades and walls, both indoors and outdoors, with the advantage of having a dual use: as a protective and thermal and acoustic insulating element, and as a decorative element.

DETAILED DESCRIPTION OF THE INVENTION

The sprayable, thermal and acoustic insulating surfacing proposed by the present invention is configured as a remarkable novelty in its field of application, the characterizing details distinguishing same being suitably described in the final claims attached hereto.

Specifically, as previously mentioned, the invention proposes an aqueous product incorporating natural cork particles and it is particularly developed for being applied with spraying equipment as a surfacing in the construction sector, especially for façades and walls or ceilings, leaving a layer with the desired thickness, which is possible as a result of having high adherence, elasticity and durability, in addition to being an excellent thermal and acoustic insulation.

That is due, in an innovative manner, to the fact that the base for the surfacing consists of a special aqueous dispersion, formed by several elements based on copolymers acrylics and other components which provide it with special adherence, resistance, elasticity, and impermeability properties, and when mixed with natural cork particles, provide it with insulating properties entailing considerable energy savings.

This sprayable surfacing based on cork furthermore includes in its composition Terbutryn with 3-iodo-2-propynyl butylcarbamate as a protecting agent for protecting the dry film against attack by microorganisms such as algae, fungi, etc.

Specifically, the special aqueous dispersion used as a base or binder with respect to the sprayable cork surfacing, comprises of the following elements in the indicated proportions:

| | |
|---|---|
| Acrylic copolymer | 31.5% |
| Polyvinyl alcohol | 5.4% |
| sodium carboxymethyl cellulose (Cellulose derivative) | 0.45% |
| ultrafine talcum powder (Laminar filler) | 6.3% |
| Wetting agents and surfactants | 0.45% |
| Preservative | 0.135% |
| Terbutryn with 3-iodo-2-propynyl butylcarbamate (Biocidal substance protecting Against attack by microorganisms) | 0.255% |
| Water | 45.54% |

From 7 to 10% of natural cork particles which can have a larger or smaller size, as desired, are added to this dispersion. The acrylic copolymer can be a monomer, acryl, butyl acrylate, methyl methacrylate. The wetting agents and surfactants is sodium alkyl ether sulfate. The preservative is a mixture of 2-methyl-2H-isothiazol-3-one and 1,2-benzisothiazol-3(2H)-one in a 1:1 proportion. The mixture of terbutryn with 3-iodo-2-propynyl butylcarbamate is provided in a 10:3 proportion.

The sprayed cork surfacing therefore has the following properties:

Specific weight: 0.91 g/cc
Solid content: 45%
Dried to the touch: 1-2 hours
Completely dried, depending on support and moisture: 8-24 hours
Minimum/maximum application temperature: +7° C./+30° C.
Maximum VOC (volatile organic compounds) content: 19 g/l
Non-toxic product
Asphalt product-free Therefore it is an advantageous product as a surfacing because it has a dual use:

As protection: In addition to the barrier effect that any paint has against external inclemency, as it contains cork particles, it has the characteristics of this material, and it is therefore also thermal and acoustic insulation, also acting as a waterproofing layer.

As decoration: The warmth and feel of natural cork provides a characteristic finish offering the possibility of multiple colors that are both natural and with water-based dyes and all being lightfast.

Furthermore, the surfacing can be applied on virtually any surface, on walls, ceilings and floors of any type.

Due to its properties, the product can be used indoors and outdoors, in homes, garages, businesses, industrial warehouses, etc.

Its most common uses are:
Water-proofing for roofs and façades
Thermal and acoustic insulation
Sealant and adhesive
Anti-moisture
Anti-niter
Asbestos encapsulation The sprayable cork surfacing is applied easily with spraying equipment, with a pressure between 3.5 and 4 atm. Each spray leaves a layer at least 3 mm thick. A double layer is recommended in roofs, using spray guns, rollers or other techniques.

The proposed cork surfacing can advantageously replace a large number of insulation materials and systems, further adding elasticity, flexibility and mechanical resistance, thermal and acoustic insulation, impermeability and protection of the dry film against attack by microorganisms.

The energy savings are estimated to be about 30-40%, accompanied by significant manual labor and material savings in comparison to conventional products and full compliance with the new European building regulations.

The described sprayable, thermal and acoustic insulating surfacing is therefore an innovation comprising constitutive technical features unknown up until now, and for these reasons combined with its practical usefulness, the proposed invention is provided with sufficient grounds to be granted the exclusive privilege sought.

The invention claimed is:

1. A sprayable, thermal and acoustic insulating surfacing applicable for surfacing façades and walls or ceilings, both indoors and outdoors, consisting of:
   a binding aqueous dispersion having:
   Acrylic copolymer;
   Polyvinyl alcohol;
   Sodium carboxymethyl cellulose;
   Ultrafine talcum powder;
   Wetting agent and surfactant;
   Preservative;
   Cork;
   a mixture of Terbutryn and 3-iodo-2-propynyl butylcarbamate; and
   Water.

2. The sprayable, thermal and acoustic insulating surfacing according to claim 1, wherein the binding aqueous dispersion comprises the following proportions by weight:
   31.5% of Acrylic copolymer;
   5.4% of Polyvinyl alcohol;
   0.45% of sodium carboxymethyl cellulose;
   6.3% of ultrafine talcum powder;
   0.45% of Wetting agent and surfactant;
   0.135% of Preservative;
   10% of cork;
   0.255% of the mixture of Terbutryn and 3-iodo-2-propynyl butylcarbamate; and
   45.54% of Water.

3. The sprayable, thermal and acoustic insulating surfacing according to claim 1, wherein said cork comprises natural cork particles.

4. The sprayable, thermal and acoustic insulating surfacing according to claim 1, wherein the wetting agent and surfactant is sodium alkyl ether sulfate.

5. The sprayable, thermal and acoustic insulating surfacing according to claim 1, wherein the preservative is a mixture of 2-methyl-2H-isothiazol-3-one and 1,2-benzisothiazol-3(2H)-one.

6. The sprayable, thermal and acoustic insulating surfacing according to claim 5, wherein said mixture of 2-methyl-2H-isothiazol-3-one and 1,2-benzisothiazol-3(2H)-one is present in a 1:1 proportion.

7. The sprayable, thermal and acoustic insulating surfacing according to claim 1, wherein the mixture of terbutryn and 3-iodo-2-propynyl butylcarbamate is present in a 10:3 proportion.

\* \* \* \* \*